United States Patent [19]

Milutinovich

[11] 4,034,485
[45] July 12, 1977

[54] COMPOSITE FACE APPARATUS AND METHOD

[75] Inventor: Savo Milutinovich, Hollywood, Calif.

[73] Assignee: Savo, Inc., Hollywood, Calif.

[21] Appl. No.: 687,902

[22] Filed: May 19, 1976

Related U.S. Application Data

[63] Continuation of Ser. No. 552,762, Feb. 24, 1975, abandoned.

[51] Int. Cl.$^2$ .......................................... G09B 1/06
[52] U.S. Cl. ...................................... 35/28; 35/53; 281/16
[58] Field of Search .................... 35/26, 28, 53, 55; 283/63 R; 281/16

[56] References Cited

U.S. PATENT DOCUMENTS

| 2,974,426 | 3/1961 | McDonald | 35/26 |
| 3,336,681 | 8/1967 | Minasy | 35/28 |
| 3,620,552 | 11/1971 | Woodcock | 281/16 X |

FOREIGN PATENT DOCUMENTS

| 623,611 | 3/1927 | France | 35/53 |
| 1,194,357 | 5/1959 | France | 281/16 |
| 829,121 | 1/1952 | Germany | 35/26 |
| 1,195,057 | 6/1965 | Germany | 35/28 |

OTHER PUBLICATIONS

Translation of German Furtmayr patent cited above.

*Primary Examiner*—Harland S. Skogquist
*Attorney, Agent, or Firm*—Woodard, Weikart, Emhardt & Naughton

[57] ABSTRACT

A plurality of stacks of opaque pages, each page bearing a unique representation of a facial part and a coded indicium, the stacks of pages being bound in a book form. The stacks of pages are arranged along the binding to represent, in order, representations of hair, eyes, nose and mouth. A witness selects the page in each stack of pages which best represents the features of a person to be identified, and the code numbers corresponding to the pages selected are relayed to other personnel having identical books with identical coding to quickly provide said other personnel with a composite facial representation of a subject. A plurality of overlays for long hair, mustaches and so forth are provided for use with the composite face, and the overlays are also coded, with similar sets of coded overlays being provided to the personnel having copies of the composite face book.

1 Claim, 6 Drawing Figures

COMPOSITE FACE APPARATUS AND METHOD

This is a continuation of application Ser. No. 552,762, filed Feb. 24, 1975, and now abandoned.

BACKGROUND OF THE INVENTION

1. Field of the Invention:

The invention is in the field of drawing, painting and sculpturing:

2. Description of the Prior Art

In the past, police departments have had a need for disseminating pictorial representations of a subject being sought to police officers in the field. This presents the further problem of assembling such a composite facial representation, which typically requires utilizing a police artist. Also, the composite facial representation which is created often must be relayed to other cities and further distances.

U.S. Pat. No. 3,353,281 to Schulze shows a transparency carrier apparatus for assembling and photocopying a facial representation. The assembly of transparent overlays disclosed in Schulze does not include the use of coded indicia for the portions of the composite face, and the apparatus is primarily for mounting the overlays for photocopying. The photocopies would then be provided, for example, to the members of a police department to assist in locating the subject of the composite. This requires physically distributing the copies to the police personnel and, in intercity distribution, would require transmission of the composite pictorial representation through some means such as a wire photo or by mail.

An assembly of overlays having the additional feature of coding of the overlay facial portions is shown in U.S. Pat. No. 2,974,426 to McDonald. The overlays shown in the McDonald patent permit a police department to assemble composite facial representations without employing artists, but the McDonald apparatus is essentially designed for use at a headquarters location rather than for field use. The overlays are coded so that for intercity distribution, the code numbers could be relayed to other headquarters of other police departments, where, using the code numbers provided and a corresponding kit of overlays, the remote police departments could assemble the same composite face as the originating police department. However, for use within the city of the originating police department, the overlay kits are not appropriate for use in the field by individual police officers because the parts of the overlay kits are easily lost and there is difficulty in assembling the overlays to obtain proper orientation of the facial features. Both the apparatus and the method for its use are intended for use at headquarters with a reasonable amount of time for the witness and the supervising police personnel to properly assemble a composite facial representation.

There has been a need for a composite face apparatus which can provide easily created composite facial representations in the field, which representations can be immediately disseminated to other police personnel in the field

SUMMARY OF THE INVENTION

One embodiment of the present invention is an apparatus for creating a likeness of a human face comprising a plurality of stacks of opaque pages, each page bearing a unique representation of a facial part and a coded indicium, the pages of a stack of said plurality of stacks bearing representations of the same facial part, the stacks being positioned relative to one another such that the representations of the facial parts of the top pages of the stacks form a composite likeness of a face, the end points of the portions of facial outlines on the pages in each stack of pages being essentially superposed, and binding means for maintaining the position of the stacks relative to one another such that the facial outline created by the top pages of the stacks of pages is essentially continuous from one stack to the next and for movably attaching the pages of each stack of pages together such that the pages of a stack of pages may be placed in a first position upon the stack and pages above a page selected to be viewed in a composite likeness may be moved to a second position not in the stack.

It is an object of the present invention to provide a composite facial representation apparatus and method easily and quickly used by police personnel in the field.

It is a further object of the present invention to provide a composite facial representation apparatus and method which enables immediate dissemination of a composite facial representation to police personnel in the field after the composite has been assembled.

Further objects and advantages of the present invention shall be apparent from the following detailed description and accompanying figures.

DESCRIPTION OF THE PREFERRED EMBODIMENT

Figure 1:
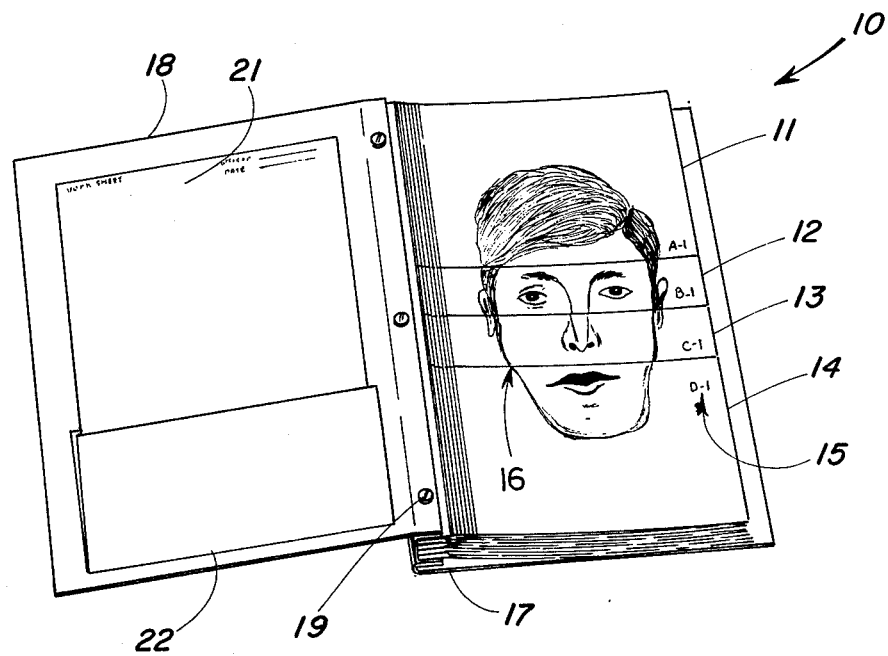
FIG. 1 is a perspective view of a composite facial representation apparatus according to the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
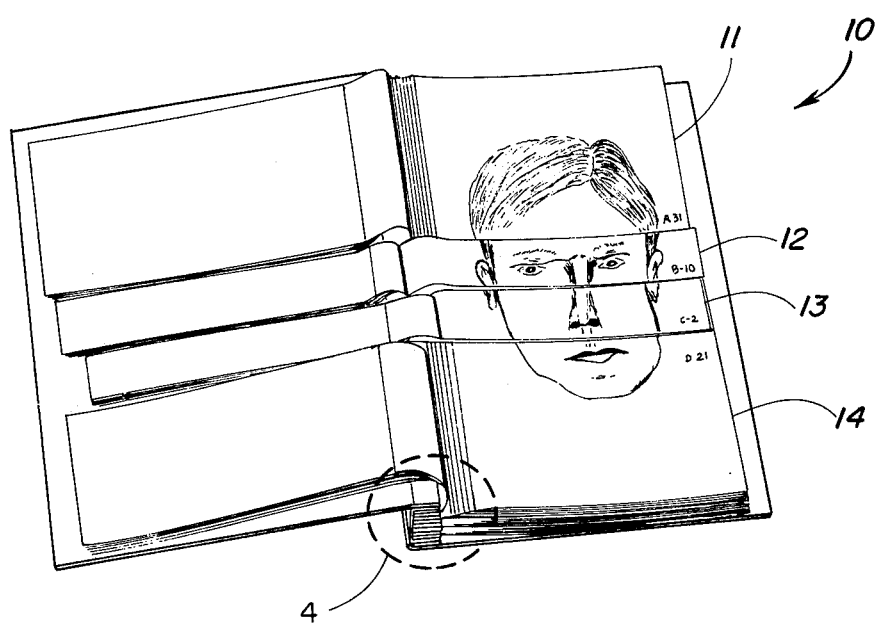
FIG. 3 is a perspective view of the apparatus of FIG. 1 with pages of the plurality of pages opened.

Referring in particular to FIGS. 1 and 3, there is shown an apparatus 10 for creating a likeness of a human face. Apparatus 10 is essentially a bound book having four adjacently mounted stacks of opaque pages. As shown, stack of pages 11 contains representations of hair styles. Stack 12 contains representations of eyes, stack 13, noses, and stack 14, mouths and chins. The pages are bound along their left-hand edges to maintain them somewhat in a book fashion with the pages of each stack of pages 11 through 14 being turnable separately. The facial lines such as the outline of the face at point 16 (FIG. 1) are drawn and mounted by the binding such that the end points are adjacent one another from one stack such as 13 to the next such as 14.

In addition, of course, to maintain this alignment despite the turning of pages, the end points of the facial outline remain generally at point 16, for example, as pages in stacks 13 and 14 are turned. A coded indicium such as 15 is provided for each page in each stack of pages, so that a selected page in the creation of a facial composite is uniquely identified.

Figure 2:
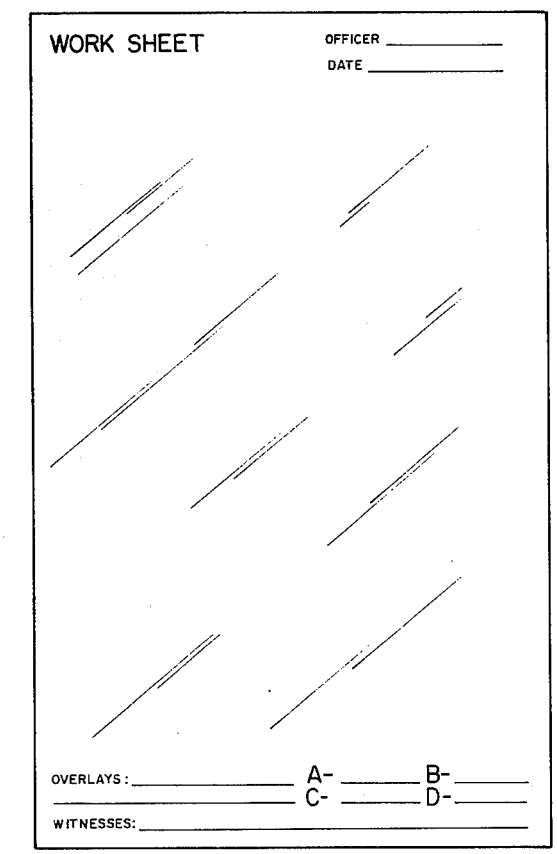
FIG. 2 is an enlarged view of a work sheet which accompanies the apparatus of FIG. 1.

Book 10 includes a front cover 18 and back cover 17 held together with standard screw fasteners such as 19. The edges of sets of pages in each of the stacks of pages are held together between covers 17 and 18 as shall be described more particularly heinafter. A work sheet 21 is carried in pocket 22 mounted on the inside of front cover 18. Work sheet 21 may alternatively be carried in the overlay book described infra. Referring to FIG. 2, work sheet 21 includes a plurality of spaces for indicating the officer and date, the coding of the pages of book 10 for a particular facial composite, coding of overlays, if any, used together with book 10, and the witnesses providing the identification information. Work sheet 21 is plastic such that the work sheet may be reused.

Figure 4:
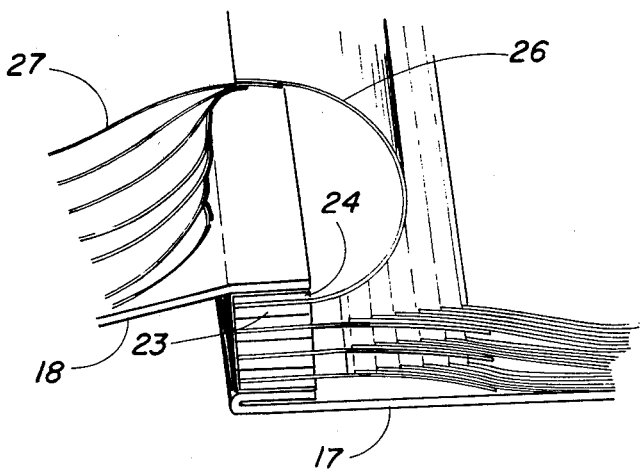
FIG. 4 is an enlarged view of the binding and page orientation of the apparatus of FIG. 3.

Referring now to FIG. 3, the book 10 of FIG. 1 is shown with a different number of pages of the plurality of pages in each stack turned over, creating a particular facial composite, such as might have been selected by a witness. As can be seen in FIG. 3, the facial parts shown are each coded as A31, B10, C2 and D21. Book 10 contains about 28 pages in each stack of pages, but greater numbers of pages, such as 50 or 60, are contemplated for greater selection purposes. The binding of stack 14 of pages is shown in greater detail in FIG. 4. As shown in FIG. 4, each set of seven pages from stack 14 is attached to a single heavy paper or cloth strip 26 which is received between binding strips 23 and 24 and held in the binding by threaded fasteners such as 19 (FIG. 1). The sets of pages may include a greater number of pages such as ten. Referring to both FIGS. 4 and 5, it can be seen that each set of pages such as page 27 is attached to connecting strip 26 which is the member which is bound in the binding of book 10.

Figure 5:
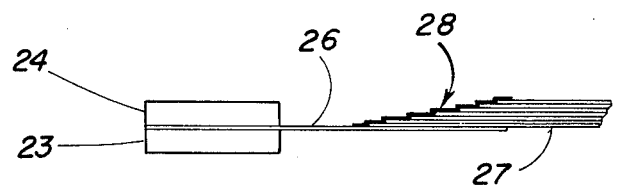
FIG. 5 is an enlarged view of one set of pages in a side or edge view.

Pages such as 27 are laid one over another with the left edges of the pages overlapping as shown best in FIGS. 4 and 5. A strip of tape such as 28 is placed over each succeeding edge of sheets 27 as shown by the darkened lines of FIG. 5. This binding arrangement facilitates the easy turning of pages without missing pages as the various alternative facial representations are viewed by a witness to assemble a composite facial representation. As shown in FIG. 3 is regard to stacks 12 and 13, when a portion of one of the above-described sets of seven pages is turned, the succeeding pages of the set are raised slightly and are easily accessible for further turning of the pages. This binding arrangement also avoids the distortion of the positioning of the outlines of the facial representations due to "pull" from the binding on the pages. As can be seen, an entire set of seven pages can be turned and they will have no "pulling" effect on unturned pages of other sets.

Figure 6:
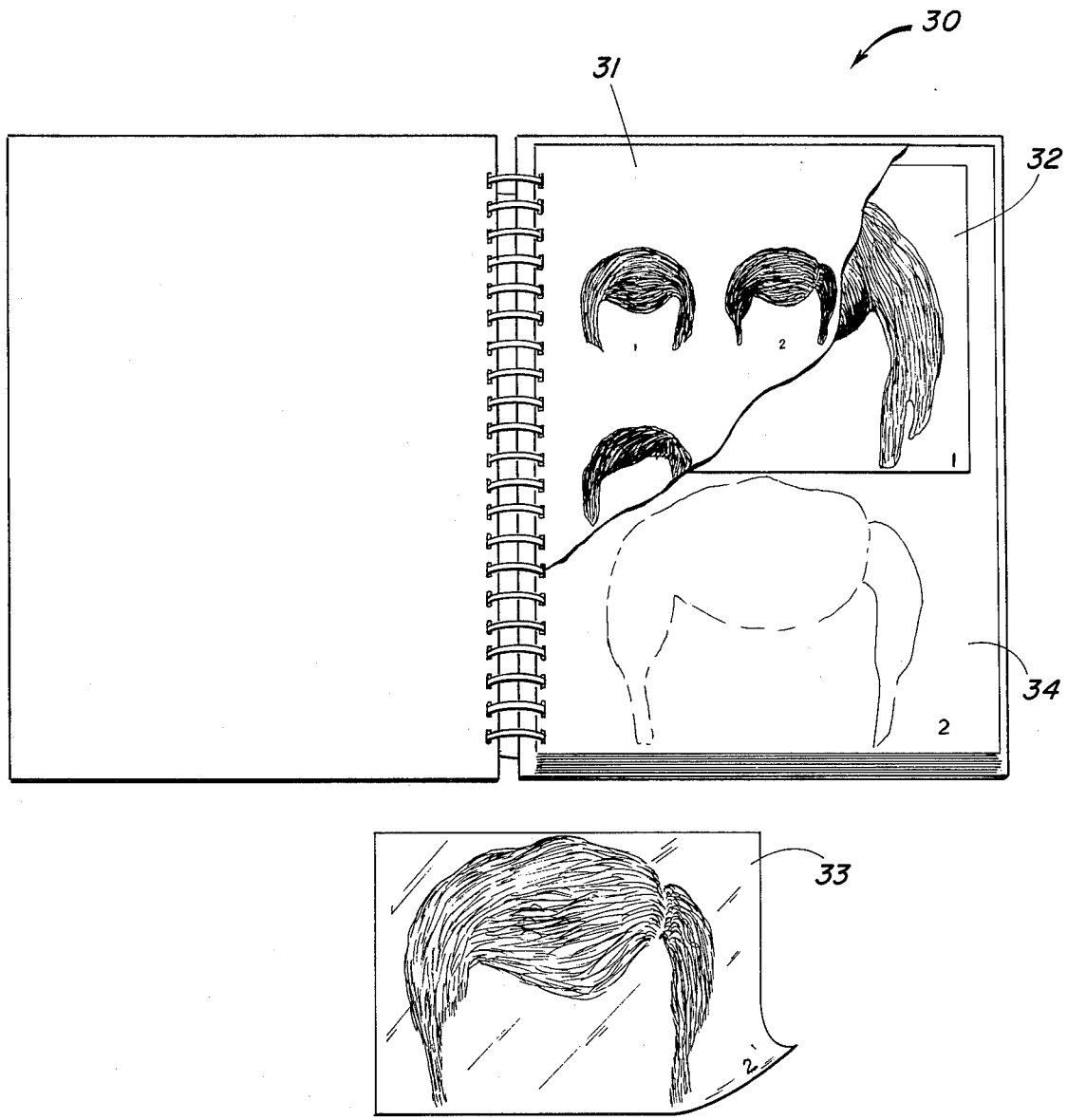
FIG. 6 is a perspective view of an overlay book for use with the apparatus of FIG. 1.

FIG. 6 shows a book of overlays for use with book 10 to provide various unusual or special facial representations. The illustrated overlays are of hair styles, but the overlay book 30 also includes overlays for scars, mustaches, beards, sideburns, eyeglasses, etc. Front pages in book 30, such as 31, show a reduced-size catalog of the overlays provided in the rear section of the book.

The overlays themselves such as 32 and 33 are plastic transparencies which are provided to be placed over composite faces assembled by using book 10. The overlays are mounted on opaque plastic pages such as 34 which contain outlines of the overlays to indicate the replacement position for each overlay. Opaque pages 34 contain representations on either side and the plastic materials of the pages 34 and overlays such as 32 and 33 are such that the overlays stick to the plastic pages. Each overlay has a code symbol which is recorded together with the set of code symbols for the composite arrived at through the use of book 10.

As can be seen, book 10 can be used to create a basic facial composite by a witness, and, if necessary, an overlay or overlays may be superimposed on the composite arrived at through the use of book 10 in order to provide a complete representation. The pages in book 10 are as described above, opaque, and the facial representations are actual artwork rather than mere outlines as found on overlays in the prior art. The use of real artistic renderings enables a witness to visualize the composite being produced much easier, and the use of such artwork more closely approximates the situation of having an artist from the composite in each case. As mentioned above, the book 10 is ideal for use by police in the field and the use of actual artwork for the facial representations facilitates the ability of the officer in the field to obtain a composite through working with a witness in the field.

As mentioned above, the officer receiving the composite information from the witness can relay the appropriate code numbers for the selected pages, and overlays if any, to other officers in the field, each of whom has a book such as 10 and is able to immediately form a composite of the suspect described by the witness without having to return to headquarters. Since the pages of apparatus 10 are mounted, as described above, in a book format, the apparatus is particularly useful in the field since pages will not be lost and no set up time is required for use of apparatus 10.

While there have been described above the principles of this invention in connection with specific apparatus, it is to be clearly understood that this description is made only by way of example and not as a limitation in the scope of the invention.

What is claimed is:

1. Apparatus for creating a likeness of a human face comprising:
   a. A plurality of stacks of opaque pages.
      1. each page bearing a unique representation of a facial part and a coded indicium,
      2. the pages of a stack of said plurality of stacks bearing representations of the same facial part,
      3. the stacks being positioned relative to one another such that the representations of the facial parts of the top pages of the stacks form a composite likeness of a face, the stacks being positioned successively adjacent one another, the edges of pages of of a stack adjacent another stack being essentially similar,
      4. The end points of the portions of facial outlines on the pages in each stack of pages being essentially superposed; and
   b. binding means for maintaining the position of the stacks relative to one another such that the facial outline created by the top pages of the stacks of pages is essentially continuous from one stack to the next and for movably attaching the pages of each stack of pages together such that the pages of a stack of pages may be placed in a first position upon the stack and pages above a page selected to be viewed in a composite likeness may be moved to a second position not in the stack, each stack of pages having a side edge, the edge edge of each page being closer to the representation of a facial part than the side edge of the page immediately below it, the binding means including means for hingedly attaching each said page edge to the page below it.

* * * * *